United States Patent [19]
Mitchell

[11] Patent Number: 6,074,208
[45] Date of Patent: Jun. 13, 2000

[54] NOISE REDUCTION IN FLUID FLOW PASSAGE

[76] Inventor: Kenneth B. Mitchell, 205- 4675 Valley Drive, Vancouver, British Columbia, Canada, V6J 4B7

[21] Appl. No.: 09/138,007

[22] Filed: Aug. 21, 1998

[51] Int. Cl.$^7$ .................................................. A61C 17/04
[52] U.S. Cl. ................................ 433/91; 433/92; 15/420; 604/902
[58] Field of Search .................................. 433/91, 92, 93, 433/94, 95, 96; 604/42, 48, 190, 902, 268; 15/420, 422; 222/189; 210/461; 137/140

[56] References Cited

U.S. PATENT DOCUMENTS

| | | | |
|---|---|---|---|
| 1,192,408 | 7/1916 | Frame . | |
| 4,158,916 | 6/1979 | Adler ........................................ | 433/91 |
| 4,265,621 | 5/1981 | McVey ...................................... | 433/91 |
| 4,538,631 | 9/1985 | Prince ..................................... | 433/91 X |
| 4,587,687 | 5/1986 | Ikonen et al. .............................. | 15/314 |
| 4,672,953 | 6/1987 | DiVito ..................................... | 433/91 X |
| 4,927,428 | 5/1990 | Richards .................................. | 433/91 X |
| 5,078,603 | 1/1992 | Cohen ...................................... | 433/91 |
| 5,151,094 | 9/1992 | Hanifl ..................................... | 433/91 X |
| 5,195,952 | 3/1993 | Solnit et al. . | |
| 5,463,792 | 11/1995 | Hogan et al. ........................... | 433/91 X |
| 5,688,121 | 11/1997 | Davis ...................................... | 433/91 X |

*Primary Examiner*—Nicholas D. Lucchesi
*Attorney, Agent, or Firm*—Elbie R. de Kock

[57] ABSTRACT

A fluid flow passage defined by a surface which surrounds the passage is provided with a plurality of projections, such as fibrils or brush like bristles, on the surface extending transversely to the flow passage. The projections serve to counteract or dampen the generation of high frequency sound energy or noise. The flow passage may be part of a medical or dental aspirator or industrial vacuum intake system or high pressure steam or gas exhaust system.

8 Claims, 3 Drawing Sheets

NOISE REDUCTION IN FLUID FLOW PASSAGE

FIELD OF THE INVENTION

This invention relates to a method and apparatus for damping or counteracting the generation of high frequency sound energy or noise by a fluid flowing through a flow passage, or an inlet or outlet orifice of such a passage, such as a fluid being drawn into a conduit under suction or exiting a conduit under pressure.

BACKGROUND OF THE INVENTION

High frequency sound energy produced by dental aspirators is a constant source of irritation, not only to the patient, but also for dental practitioners exposed thereto for long periods of time and may cause hearing problems, stress and fatigue.

A dental aspirator comprises a suction tube, the free end of which is inserted into a patient's mouth to remove water, saliva and solid material from the patient's mouth. High frequency sound energy or noise is generated by the air or air/liquid mixture being drawn into the intake orifice and forced down the suction tube of the aspirator.

The problem also arises in other areas of dental/medical practise, such as surgical vacuum systems used for the removal of air/liquid/blood during surgery, as well as laser fume extraction systems.

Apart from the noise which is generated, a further problem which arises is that of "suck back", which occurs when the suction orifice is blocked by tissue in or around the operation site. Since this can result in bacterial and viral cross-infection, it has become a cause for concern in medicine and dentistry.

In addition to the above examples given in respect of the medical field, noise reduction is also important in other areas, such as in industrial applications, e.g. vacuum intake or exhaust systems, as well as high pressure steam exhaust systems and high frequency sound energy associated with jet engines.

SUMMARY OF THE INVENTION

According to the invention there is provided a fluid flow passage defined by a surface which surrounds the passage and provided with a plurality of projections on the surface extending transversely to the flow passage.

The projections may extend around substantially the entire inner periphery of the flow passage.

The flow passage may be substantially circular in cross section, the projections extending radially relative thereto.

The projections may be of a flexible material. They may be of any suitable size or shape. They may, for example, be in the form of fibrils, such as small filaments or fibres or they may be in the form of brush like bristles or hairs or any other larger or smaller type of projection or protrusion which effectively increases the surface area of a fluid flow passage or inlet or outlet orifice of a fluid flow passage. The increase in surface area so achieved alters the turbulence and rapid oscillating motion of the medium in intake and exhaust systems which cause intense directional sound peaks. This results in sound damping.

The invention also extends to an aspirator or surgical vacuum system, such as used in the medical or dental fields, incorporating a fluid flow passage provided with projections, as described.

The invention further extends to an industrial vacuum intake system as well as a high pressure steam or gas exhaust system incorporating a fluid flow passage provided with projections, as described.

Also according to the invention there is provided a method of damping or counteracting noise in a fluid flow passage comprising the step of providing a plurality of flexible projections extending transversely of the flow passage.

Also according to the invention there is provided a method of counteracting trauma to living tissue, comprising the step of providing a plurality of flexible projections on a vacuum intake orifice which is brought into contact with said tissue.

Also according to the invention there is provided a method of counteracting the phenomenon of suck back in a vacuum line, comprising the step of providing a plurality of projections on an intake orifice of said vacuum line, to thereby counteract complete closure of the orifice.

Also according to the invention there is provided a method of facilitating the removal of debris during surgery comprising the step of providing a plurality of projections on an intake orifice of a surgical vacuum system used during said surgery.

Also according to the invention there is provided a method of reducing resonance in a resonating cavity comprising the step of providing a plurality of projections inside the cavity to reduce the size of the cavity.

Further according to the invention there is provided an aspirator or vacuum suction tube comprising a tube having a front end defining an intake orifice and a rear end for connection to a source of suction; and a plurality of transverse projections on an inside surface of the tube at the front end of the tube.

Further objects and advantages of the invention will become apparent from the description of a preferred embodiment of the invention below.

BRIEF DESCRIPTION OF THE DRAWINGS

The invention will now be described, by way of examples, with reference to the accompanying drawings, in which.

DETAILED DESCRIPTION OF PREFERRED EMBODIMENTS

Figure 1:
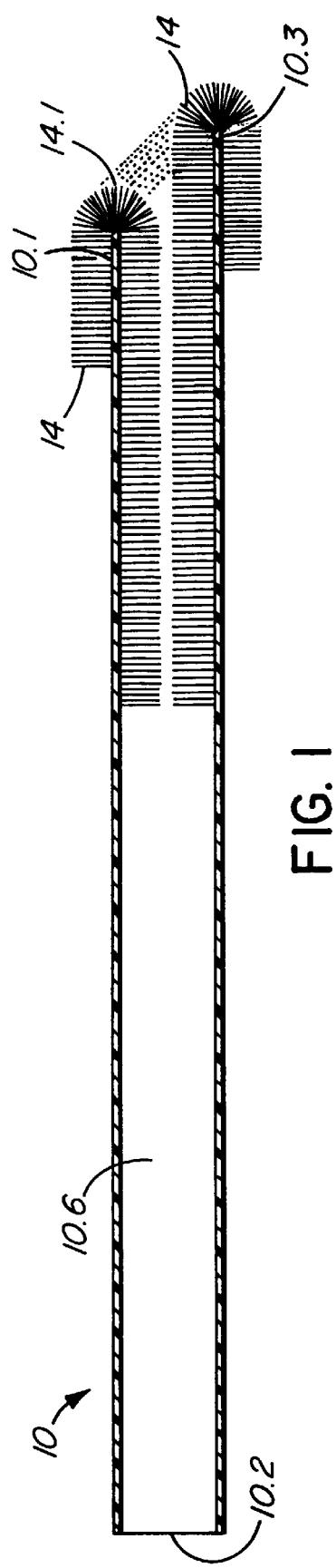
FIG. 1 is a cross-sectional side view of an evacuation tube which is suitable for use as an aspirator in dentistry or surgery, provided with sound damping projections thereon, according to one embodiment of the invention.
Figure 2:
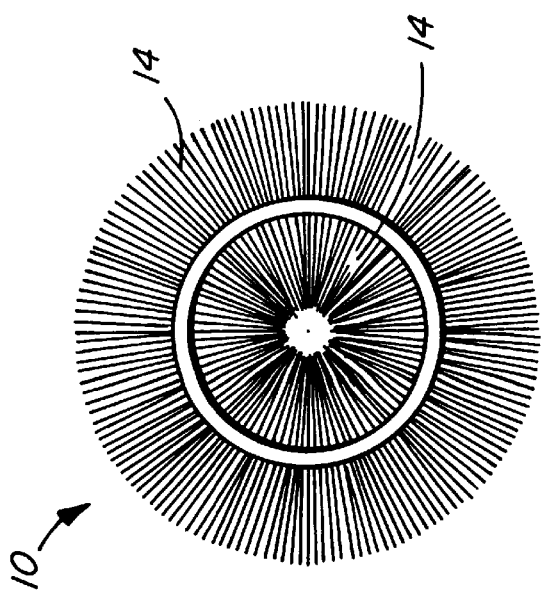
FIG. 2 is a front end view of the evacuation tube of FIG. 1.

In FIGS. 1 and 2, reference numeral 10 generally indicates an evacuation tube or aspirator for use in dentistry or surgery. The tube 10 has a front end 10.1, which serves as an intake orifice and a rear end 10.2 which, in use, is connected to a source of suction, such as a vacuum.

The tube 10 is of a disposable, tissue-tolerant, non allergenic plastic material. In the present example, the external diameter of the tube is 11 mm to fit standard dental vacuum adaptors. The length is conveniently about 15 cm. As shown, the rear end 10.2 is cut at right angles, whereas the front end is cut at a bevel of 45° to form a suction lip 10.3.

Figure 3A:
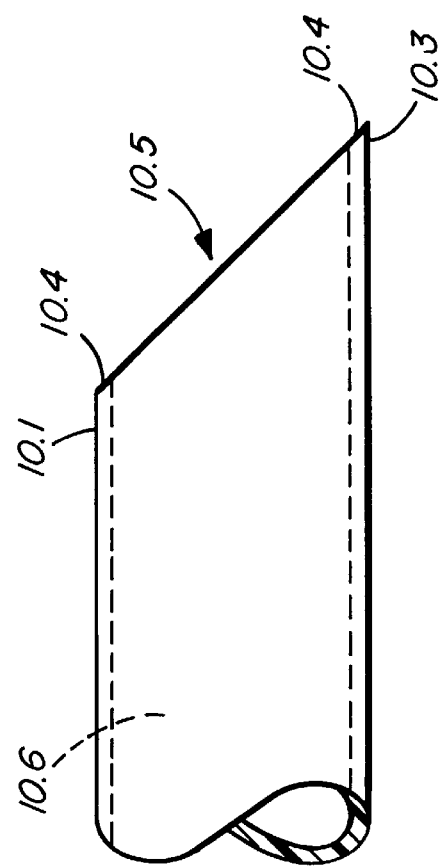
FIGS. 3A and 3B are side and end views, respectively, of the tube of FIG. 1 but with the sound damping projections omitted for illustration purposes.

The suction lip 10.3 is more clearly shown in FIG. 3A illustrating the front end 10.1 of the tube 10, but with the bristles (referred to below) omitted for the sake of clarity.

The front end 10.1 is provided with fine plastic brush like projections or bristles 14. The bristles 14 are provided on the outside surface of the tube 10 along a distance of about 1.5 cm from the tip of the tube 10, and on the inside surface extending up to about 5 cm from the tip of the tube 10. The bristles also extend from the surface 10.4 forming the face of the intake orifice 10.5, as shown at 14.1.

Figure 3B:
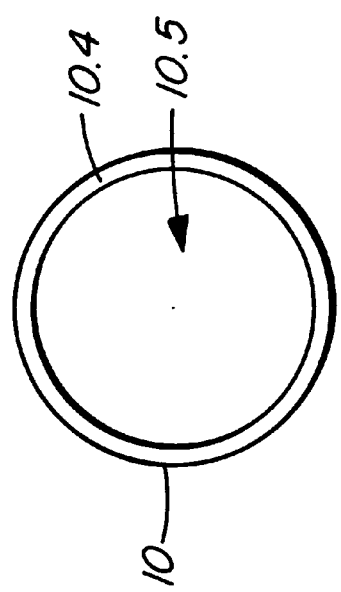

The intake orifice 10.5 and the surface 10.4 forming the face of the orifice 10.5 are more clearly shown in FIG. 3B, which is a front end view of the tube 10, but again with the bristles 14 omitted for the sake of clarity.

In use as a dental aspirator, suction is applied to the tube 10 and it is inserted in to a patient's mouth. As air, water, saliva and other dental debris flows into the orifice 10.5 at the front end 10.1 and through the flow passage 10.6 defined by the tube 10, the high frequency sound caused by shear layer turbulence of air or air/liquid mixture being forced across an orifice or sharp edge at high speed, is dampened by the flexible bristles 14 which increase the surface area over which the air/liquid mixture flows.

The soft pliable projections or bristles 14 serve to increase the surface area sufficiently to dampen the noise without obstructing the flow passage 10.6 to the flow of fluid and solid material there through.

The projections 14 at the suction orifice 10.5 are firm enough to suspend the suction tip 10.3 above the operation site so as to avoid or counteract suction attachment of the suction orifice 10.5 to body tissue, thus rendering the suction tip 10.3 atraumatic. This reduces tissue damage and bruising caused iatrogenically by the running edge of the suction tip 10.3 on anaesthetized tissue.

A further advantage is that the projections can effect a brushing action which can be used, for example, to remove detritus that has adhered to dried mucous membranes. This brushing action can also be employed to remove solid waste matter, such as bone chips or excess restorative material from the mouth.

Figure 5:
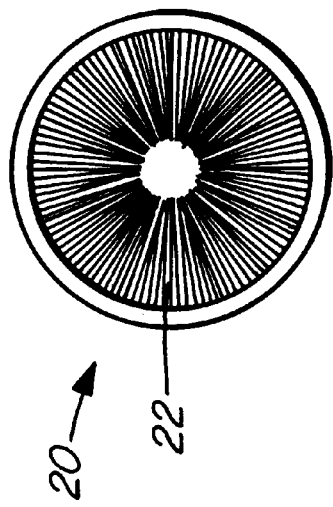
FIG. 5 is an end view of the tube of FIG. 4.
Figure 4:
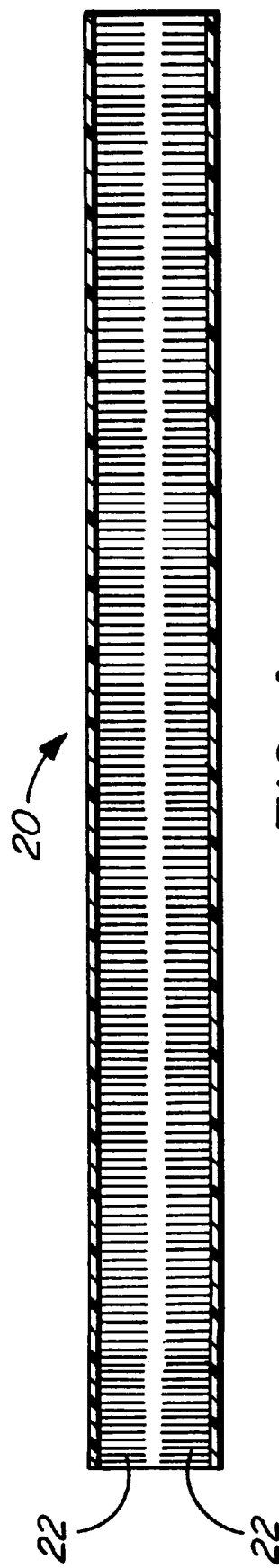
FIG. 4 is a cross-sectional side view of an air or steam exhaust pipe which is suitable for use in industrial applications according to another embodiment of the invention.

In FIGS. 4 and 5, reference numeral 20 generally indicates an exhaust pipe for high pressure air or steam.

The pipe 20 is provided with radially extending brush like projections or bristles 22 on its inside surface. As in the case of the tube 10 of FIGS. 1 and 2, the projections 22 serve to increase the surface area to dampen the noise created by the exhausting steam or air without obstructing the flow passage to such an extent that the exhaust system becomes ineffective. The length of the pipe 20 may be varied as required depending on the type of application.

Figure 6:
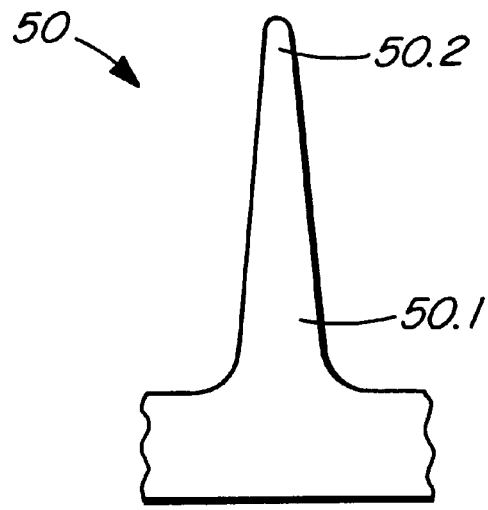
FIGS. 6 to 8 are side views showing examples of projections for noise reduction in flow channels.

In FIG. 6 reference numeral 50 generally indicates one example of a projection. As shown, the projection 50 is tapered from its base 50.1 to its tip 50.2. This may be particularly useful when used in an aspirator. Due to its greater thickness, the base 50.2 of the projector 50 is sufficiently firm to counteract or prevent the suction orifice to become completely blocked by tissue in or around the operation site. This, therefore, counteracts the phenomenon of "suck back" which occurs if the suction orifice in an air or liquid vacuum line is blocked.

Figure 7:
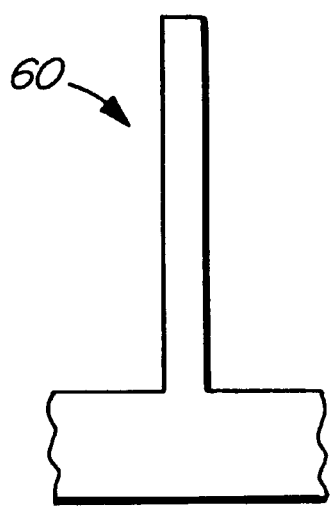
Figure 8:
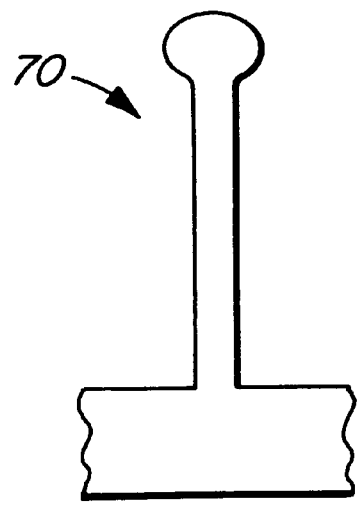

Apart from the tapered configuration of the projection 50 in FIG. 5, the projections may be of uniform diameter or rod-like, as indicated at 60 in FIG. 7, or they may be provided with enlargements at their tips, as shown at 70 in FIG. 8 to further increase surface area and reduce sharp edges.

The projections may further be of any suitable shape or cross-section, such as round, oval shaped, rectangular, square or triangular.

While only preferred embodiments of the invention have been described herein in detail, the invention is not limited thereby and modifications can be made within the scope of the attached claims.

What is claimed is:

1. An aspirator or vacuum suction tube comprising a tube defining a fluid flow passage having a front end defining an intake orifice and a rear end for connection to a source of suction, the tube further having an inside surface and an outside surface and provided with a plurality of projections, at least some of which extend transversely of the fluid flow passage, said projections extending from the inside surface of the tube over the intake orifice and onto the outside surface at the front end of the tube.

2. The aspirator or vacuum suction tube according to claim 1, wherein the projections extend around substantially the entire inner periphery of the flow passage.

3. The aspirator or vacuum suction tube according to claim 1, wherein the flow passage is substantially circular in cross section and at least some of the projections extend radially relative thereto.

4. The flow passage according to claim 3, wherein the projections are of a flexible material.

5. The aspirator or vacuum suction tube according to claim 1, wherein the projections are tapered.

6. The aspirator or vacuum suction tube according to claim 1, wherein flexible projections are provided on the tube extending longitudinally forwardly of said intake orifice.

7. A method of damping or counteracting noise in a fluid flow passage having an intake orifice and an inside and outside surface, comprising the step of providing a plurality of projections extending from said inside surface over the intake orifice and onto said outside surface, at least some of which projections extend transversely of fluid flow passage.

8. The method according to claim 7 wherein the projections are flexible.

* * * * *